United States Patent
Huebner et al.

(10) Patent No.: US 8,518,090 B2
(45) Date of Patent: Aug. 27, 2013

(54) FASTENER WITH SERRATED THREAD FOR ATTACHMENT TO A BONE PLATE AT A SELECTABLE ANGLE

(75) Inventors: Randall J. Huebner, Portland, OR (US); David W. Van Vleet, Hillsboro, OR (US); Rudolph A. Ventura, Beaverton, OR (US); Jennifer R. Zuba, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 128 days.

(21) Appl. No.: 13/246,687

(22) Filed: Sep. 27, 2011

(65) Prior Publication Data

US 2012/0083847 A1   Apr. 5, 2012

Related U.S. Application Data

(60) Provisional application No. 61/390,121, filed on Oct. 5, 2010.

(51) Int. Cl.
*A61B 17/80* (2006.01)

(52) U.S. Cl.
USPC .................. 606/291; 606/281; 606/305

(58) Field of Classification Search
USPC ................................................. 606/289, 291
See application file for complete search history.

(56) References Cited

U.S. PATENT DOCUMENTS

| | | | |
|---|---|---|---|
| 6,296,642 B1 | 10/2001 | Morrison et al. | |
| 6,322,562 B1 | 11/2001 | Wolter | |
| 6,440,135 B2 | 8/2002 | Orbay et al. | |
| 6,730,091 B1 | 5/2004 | Pfefferle et al. | |
| 6,974,461 B1 | 12/2005 | Wolter | |
| 7,695,502 B2 | 4/2010 | Orbay et al. | |
| 8,337,535 B2 | 12/2012 | White et al. | |
| 2004/0261688 A1 | 12/2004 | MacGregor et al. | |
| 2006/0149265 A1 | 7/2006 | James et al. | |
| 2007/0083207 A1* | 4/2007 | Ziolo et al. ............ | 606/73 |
| 2008/0300637 A1 | 12/2008 | Austin et al. | |

FOREIGN PATENT DOCUMENTS

| | | |
|---|---|---|
| DE | 4343117 C2 | 11/1999 |
| EP | 1767160 A3 | 4/2008 |
| EP | 1996120 A2 | 12/2008 |
| EP | 2207491 A1 | 7/2010 |
| EP | 2248479 A1 | 11/2010 |
| WO | 2009058969 A1 | 5/2009 |

OTHER PUBLICATIONS

U.K. Intellectual Property Office, Patents Act 1977: Combined Search and Examination Report under Sections 17 and 18(3), U.K. Patent Application Serial No. GB1117016.4; dated Jan. 9, 2012.

* cited by examiner

*Primary Examiner* — Andrew Yang
(74) *Attorney, Agent, or Firm* — Kolisch Hartwell, P.C.

(57) ABSTRACT

Bone plate system, including methods and apparatus, for attaching a fastener to a bone plate at a selectable angle. In an exemplary method, a bone plate and a fastener may be selected. The bone plate may define an aperture having an internal thread. The fastener may include a proximal region and a distal region. The proximal region may be tapered conically toward the distal region. The fastener may be disposed in the aperture and in bone, such that the serrated thread is cross-threaded with the internal thread to create an interference fit and locked engagement of the proximal region with the aperture.

24 Claims, 4 Drawing Sheets

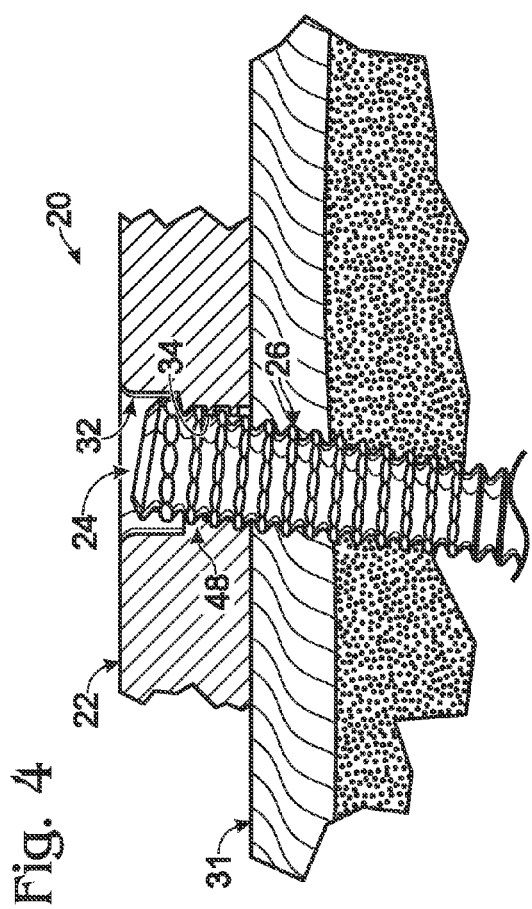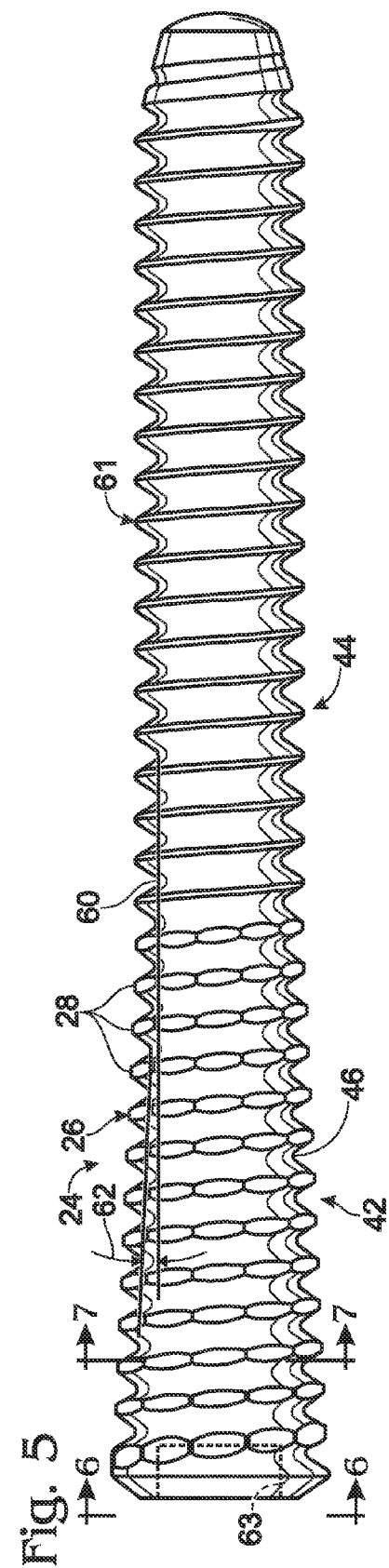

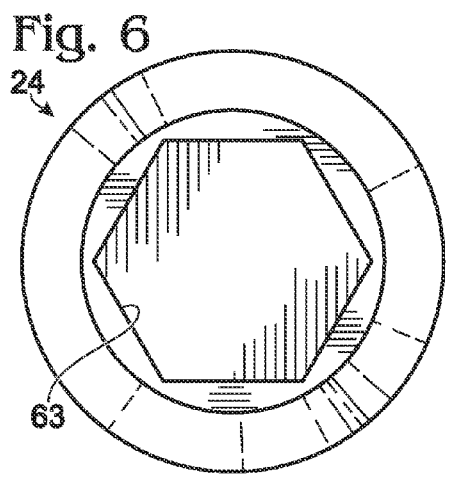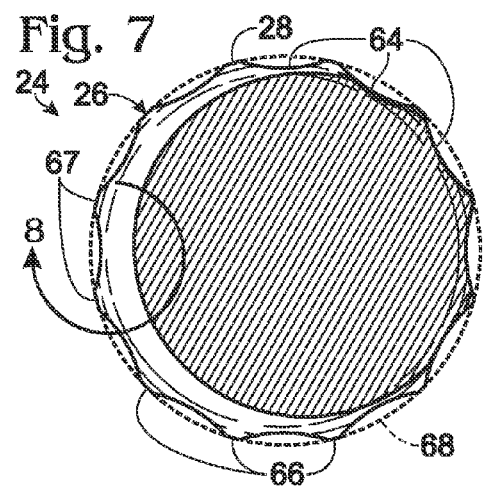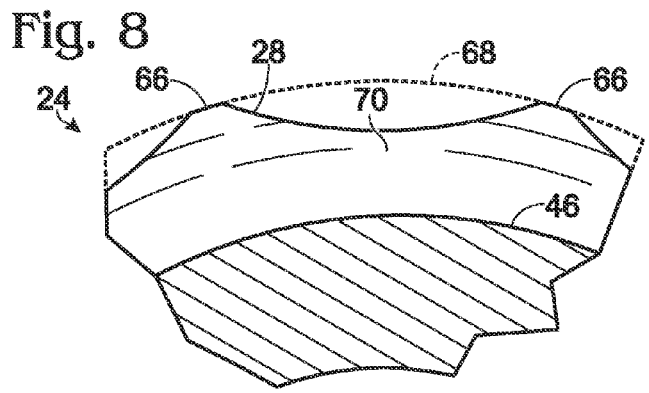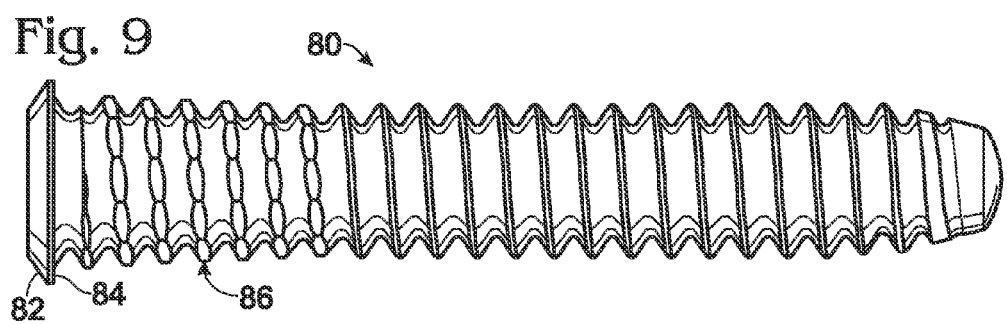

FASTENER WITH SERRATED THREAD FOR ATTACHMENT TO A BONE PLATE AT A SELECTABLE ANGLE

CROSS-REFERENCE TO PRIORITY APPLICATION

This application is based upon and claims the benefit under 35 U.S.C. §119(e) of U.S. Provisional Patent Application Ser. No. 61/390,121, filed Oct. 5, 2010, which is incorporated herein by reference in its entirety for all purposes.

INTRODUCTION

The human skeleton is composed of 206 individual bones that perform a variety of important functions, including support, movement, protection, storage of minerals, and formation of blood cells. To ensure that the skeleton retains its ability to perform these functions, and to reduce pain and disfigurement, bones that become fractured should be repaired promptly and properly. Typically, a fractured bone is treated using a fixation device, which reinforces the fractured bone and keeps it aligned during healing. Fixation devices may take a variety of forms, including casts and fixators for external fixation, and bone plates, intramedullary rods, and bone screws for internal fixation, among others.

Bone plates are implants that may be positioned under skin and other soft tissue for mounting on bone to span a fracture or other bone discontinuity. These plates may be manufactured and/or custom bent for mounting to particular regions of bone. To use a bone plate to stabilize a fractured bone, a surgeon may fasten the plate to the bone on opposite sides of the fracture using suitable fasteners, such as bone screws, so that fragments of the bone are fixed in position.

Bone plates generally include a plurality of apertures sized and shaped to receive fasteners, such as bone screws. Each aperture of a bone plate may or may not include an internal thread that permits an externally threaded bone screw to lock to the aperture when installed. When the bone screw is locked to the aperture, axial movement of the bone screw relative to the aperture is restricted. In other words, the locked bone screw generally resists being pushed farther into the aperture or being pulled out of the aperture unless the bone screw is turned.

Locked engagement of a bone screw with an aperture of a bone plate may be preferred in many fixation situations because the bone screw is less likely to back out and relies less on bone quality to fix bone. However, use of a locked bone screw typically does not allow a surgeon to choose the angle at which the bone screw is placed into bone, because the angle is established during manufacture of the bone plate. Accordingly, the surgeon cannot customize the trajectory of bone screw insertion for a particular patient's anatomy or indication.

A bone plate system disclosed in German Patent No. DE 4343117 involves a bone screw cross-threaded into an aperture of a bone plate at a selectable angle. The bone screw has a spherical head with an external thread, which is received in an internally threaded aperture that is cylindrical, conical, or spherical. However, the bone plate system of the '117 patent may be inadequate for various reasons, such as instability of the bone screw under load (i.e., the bone screw may wiggle and/or unlock), protrusion of the bone screw above the bone plate after installation of the bone screw at most angles, and/or difficulty of installation. Therefore, an improved bone plate system is needed that provides stable, locked engagement of a bone screw with a bone plate at a selectable angle.

SUMMARY

The present disclosure provides a bone plate system, including methods and apparatus, for attaching a fastener to a bone plate at a selectable angle. In an exemplary method, a bone plate and a fastener may be selected. The bone plate may define an aperture having an internal thread. The fastener may include a proximal region and a distal region. The proximal region may be tapered conically toward the distal region. The fastener may be disposed in the aperture and in bone, such that the serrated thread is cross-threaded with the internal thread to create an interference fit and locked engagement of the proximal region with the aperture.

BRIEF DESCRIPTION OF THE DRAWINGS

FIG. 4 is a sectional view of the bone plate system of FIG. 1, taken as in FIG. 3, but with the bone screw skewed with respect to the aperture, such that the serrated external thread is cross-threaded with an internal thread of the aperture, in accordance with aspects of the present disclosure.

FIG. 5 is a side view of the bone screw of FIG. 1.

FIG. 6 is an end view of the bone screw of FIG. 5, taken generally along line 6-6 of FIG. 5.

FIG. 7 is a cross-sectional view of the bone screw of FIG. 5, taken generally along line 7-7 of FIG. 5.

FIG. 8 is a fragmentary sectional view of the bone screw of FIG. 5, taken generally at the region indicated by "8" in FIG. 7.

FIG. 9 is a side view of another exemplary bone screw that may be utilized in the bone plate system of FIG. 1, in accordance with aspects of the present disclosure.

DETAILED DESCRIPTION

Figure 1:
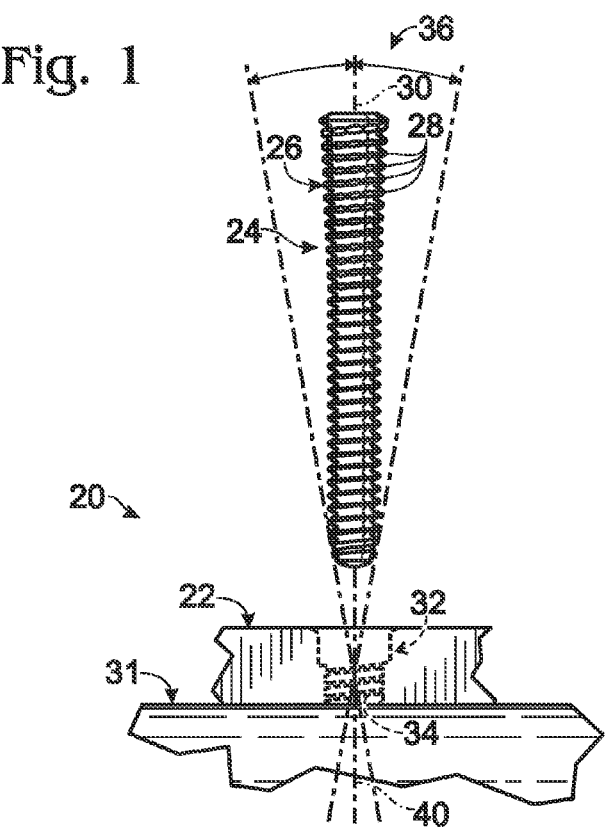
FIG. 1 is a fragmentary exploded view of selected aspects of an exemplary bone plate system including a bone plate disposed on bone, and a bone screw with a serrated external thread that locks to an aperture of the bone plate at a selectable angle, in accordance with aspects of the present disclosure.

The present disclosure provides a bone plate system, including methods and apparatus, for attaching a fastener to a bone plate at a selectable angle. In an exemplary method, a bone plate and a fastener may be selected. The bone plate may define an aperture having an internal thread. The fastener may include a proximal region and a distal region. The proximal region may be tapered conically toward the distal region. The fastener may be disposed in the aperture and in bone, such that the serrated thread is cross-threaded with the internal thread to create an interference fit and locked engagement of the proximal region with the aperture.

A method of attaching a fastener to a bone plate is provided. In the method, a bone plate and a fastener may be selected. The bone plate may define an aperture including a threaded region having an internal thread. The fastener may define a long axis and may include a proximal region and a distal region. The proximal region may be tapered conically toward the distal region. In some cases, the threaded region of the aperture may have a smaller angle of taper than the proximal region of the fastener, such that the proximal region is wedged into the threaded region when the fastener is advanced into the aperture. In some cases, the proximal region may have an angle of taper toward the distal region of about one to five degrees with respect to the long axis. The proximal region may include a serrated thread. In some cases, the serrated thread may be configured to provide threaded engagement with the internal thread without cross-threading, if the fastener is arranged coaxially with the aperture. The distal region may include another thread and may be cylindrical. The fastener may be disposed in the aperture and in bone, such that the serrated thread is cross-threaded with the internal thread to create an interference fit and locked engagement of the proximal region with the aperture.

A system for bone fixation is provided. The system may comprise a bone plate and a fastener. The bone plate may define an aperture having a threaded region including an internal thread. The fastener may define a long axis and may include a proximal region and a distal region. The proximal region may be tapered conically toward the distal region with a larger angle of taper than the threaded region and/or with an angle of taper of about one to five degrees with respect to the long axis. The fastener may include a serrated thread. The fastener may be insertable into the aperture in a coaxial arrangement with the aperture to achieve threaded engagement of the serrated thread with the internal thread without cross-threading. The fastener also may be insertable in a skewed arrangement to provide an interference fit and locked engagement of the proximal region with the aperture by cross-threading the serrated thread and the internal thread.

The use of a fastener having a taper angle of about one to five degrees and/or including a serrated thread may offer substantial advantages over other approaches to cross-threading an externally threaded fastener with an internally threaded aperture of a bone plate. For example, an angle of taper of about one to five degrees may allow the fastener to engage the bone plate aperture more effectively than with less or more of a taper. The angle is sufficiently large to form an effective wedge, but small enough to allow the fastener to advance substantially into the aperture, to increase the area of engagement and to avoid substantial protrusion of the fastener out of the top of the aperture (i.e., protrusion from the outer surface of the bone plate). As another example, the serrated thread may facilitate cross-threading better than other types of threads by creating deformable teeth along the serrated thread.

These and other aspects of the present disclosure are described in the following sections: (I) exemplary bone plate system, (II) exemplary fixation and attachment methods, and (III) examples.

I. EXEMPLARY BONE PLATE SYSTEM

This section describes an exemplary bone plate system 20 including a bone plate 22 and a fastener, namely, a bone screw 24, having an external serrated thread 26 that locks the bone screw to the bone plate at a selectable angle; see FIGS. 1-8.

A serrated external thread is any external thread that forms a plurality of teeth and/or notches along the thread through variations in thread height and/or gaps in the thread along each full winding or revolution 28 of the serrated thread around a long axis 30 defined by the fastener. The serrated thread may form any suitable number of teeth and/or notches per winding/revolution (e.g., at least about 4, 6, 8, or 10 teeth and/or notches). In some embodiments, the teeth may be at least generally pointed in profile (i.e., if viewed generally orthogonal to a flank of the thread, such as in a direction parallel to a screw axis of the thread and/or in a direction parallel to long axis 30 of the fastener).

FIG. 1 shows bone plate 22 disposed on a surface region of bone 31. The bone plate may define a plurality of apertures for receiving fasteners that secure the bone plate to bone 31. The apertures may include at least one aperture 32 including an internal thread 34. The internal thread may have the same handedness as the serrated thread, such as both being right-handed threads or both being left-handed threads.

Aperture 32 may receive a fastener, such as bone screw 24, such that the fastener is in locked engagement with the bone plate at an angle selected from a range of permitted angles, indicated at 36. In particular, bone screw 24 may be placed coaxially in the aperture such that long axis 30 of the bone screw is coincident with an axis 40 defined by aperture 32, particularly a helical axis defined by internal thread 34. With this coaxial arrangement, the external and internal threads fit together in threaded engagement without substantial cross-threading. Alternatively, bone screw 24 may be placed off-axis (non-coaxially) in aperture 32, that is, in a skewed arrangement, such that the external and internal threads engage one another in a cross-threaded configuration that also locks bone screw 24 to bone plate 22. Cross-threading occurs when the external and internal threads are not aligned with each other, such as when the threads cross one another and/or are deformed substantially by engagement with one another. The bone screw may be placed into locked engagement with the aperture over any suitable range of angles, such as up to at least about 10 or 20 degrees off-axis, among others.

Figure 2:
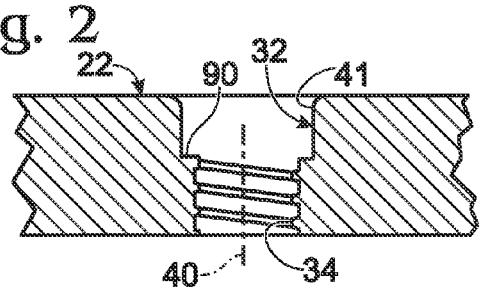
FIG. 2 is a sectional view of the bone plate of FIG. 1 taken through the aperture in the absence of bone and the bone screw.

FIG. 2 shows a sectional view of bone plate 22 taken through aperture 32. The aperture may include an upper region forming a counterbore 41 and a lower region equipped with internal thread 34. Each of the upper and lower regions may (or may not) be cylindrical. The lower region thus may be formed by a cylindrical bore having a helical ridge formed thereon. Alternatively, the upper and lower regions may, for example, be oblong if the aperture is elongated perpendicular to axis 40. Internal thread 34 may extend around aperture axis 40 any suitable number of times, such as at least about one, two, or three windings, among others.

Figure 3:
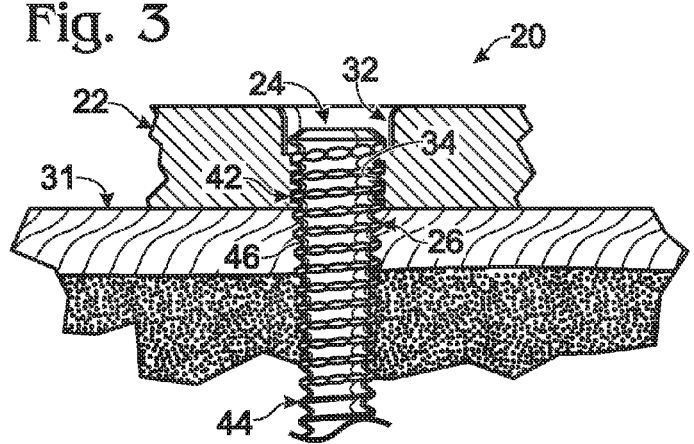
FIG. 3 is a sectional view of the bone plate system of FIG. 1, with the bone plate sectioned as in FIG. 2, and with the bone screw locked coaxially to the aperture without cross-threading, in accordance with aspects of the present disclosure.

FIG. 3 shows system 20 with bone screw 24 locked coaxially to aperture 32, without cross-threading. Serrated external thread 26 and internal thread 34 may have the same pitch, to allow the threads to mesh in alignment. Also, serrated thread 26 may be formed on a proximal region 42 that tapers toward a distal region 44 of the bone screw. Proximal region 42, including serrated thread 26 and/or a root portion 46 on which serrated thread 26 is formed, may be conical in shape. As a result, proximal region 42 may be wedged into aperture 32 as the bone screw is advanced. Accordingly, if bone screw 24 is oriented coaxially to aperture 32, serrated thread 26 and/or proximal region 42 may engage aperture 32 more tightly closer to the proximal end of internal thread 34. Furthermore, a suitable stopping point for advancement of bone screw 24 into the aperture may be identified by the surgeon during installation based on the amount of torque needed to turn the screw. (The wedge effect increases the torque needed as the screw is advanced.) Alternatively, or in addition, a suitable stopping point for advancement of the bone screw may be result from abutment of the plate with a stop structure, such as a flange, formed near a proximal end of the bone screw (e.g., see Example 1).

Bone screw 24 may extend into bone when installed. For example, distal region 44 and, optionally, an adjacent, distal portion of proximal region 42 may be disposed in bone. Either or both of regions 42, 44 may be disposed in threaded engagement with bone.

FIG. 4 shows system 20 with bone screw 24 installed off-axis in aperture 32 of bone plate 22. Serrated thread 26 may be cross-threaded with internal thread 34, which results in deformation of a portion of the serrated thread (e.g., one or more teeth thereof), a portion of aperture 32 (e.g., at least part of internal thread 34), or both. In the present illustration, deformation, which is indicated at 48, occurs more on the left side of the aperture in FIG. 4 than on the right side because the bone screw is angled in that direction. The serrated thread facilitates cross-threading and deformation of the external thread.

FIG. 5 shows bone screw 24 in a magnified view. The bone screw may include a shaft 60 with at least one external thread formed thereon. For example, serrated thread 26 may be formed on root portion 46 of shaft 60 in proximal region 42. Also, a distal thread 61 may be formed on a distal portion of the shaft 60 in distal region 44. In any event, the shaft may taper in proximal region 42, distal region 44, or both. In the depicted embodiment, shaft 60 is cylindrical in distal region 44 and conical in proximal region 42 to form root portion 46.

External threads 26, 61 of bone screw 24 may have any suitable structure. The external threads may be serrated only in proximal region 42 or only a portion thereof, such that distal thread 61 is not serrated substantially, or may be serrated in both proximal and distal regions 42, 44. Also, serrated thread 26 may be continuous with at least one nonserrated thread that also is disposed in proximal region 42 (e.g., with a nonserrated thread proximal and/or distal to the serrated thread in the proximal region 42). In some cases, threads 26, 61 may be at least generally continuous with each other by extending along different parts of the same helical path, as shown here, and may have the same pitch. Also, one or both of threads 26, 61 may have a constant pitch or a pitch that is variable (e.g., continuously variable and/or that is smaller toward the proximal (trailing) end of the bone screw). In some cases, the bone screw may have discrete threads following different helical paths and formed on respective proximal and distal regions of the shaft (e.g., see Example 2).

Proximal region 42 may have any suitable angle 62 of taper relative to the long axis of the screw. (Here, angle 62 is illustrated with respect to an axis that is parallel to the long axis.) The angle of taper may be selected to permit the bone screw to advance sufficiently into the aperture to minimize protrusion above the bone plate and to develop a sufficiently large contact area with the walls of the aperture, to lock the screw more tightly to the bone plate. Exemplary angles that may be utilized include an angle of less than about five degrees, about one to five degrees, about two to four degrees, about two to three degrees, or about 2.5 degrees, among others. Generally, angles of greater than about five degrees are less effective because these more aggressive taper angles block the fastener from advancing sufficiently into the aperture, which reduces the contact area. As a result, the fastener is more likely to loosen or pull out. Also, angles of less than about one degree also are less effective because the wedge formed by the proximal region of the fastener becomes too insubstantial to produce very tight engagement.

FIG. 6 shows an end view of bone screw 24. The proximal end of the screw may define a driver-engagement structure, such as a hexagonal socket 63, to receive a driver that turns the screw (also see FIG. 5). The screw may or may not be cannulated.

FIG. 7 shows a profile view of one complete winding 28 of serrated thread 26 about the long axis of the screw. The serrated thread may define a series of notches 64 that form a corresponding series of teeth 66 arranged along the external thread. Each tooth may have a top 67 where a height of the tooth is at a maximum for the tooth. The tops of all of the teeth of serrated thread 26 may collectively represent only a minority (less than one-half) of the total length of the serrated thread as measured along a path followed by the serrated thread around the long axis. Stated differently, the serrated thread may form a series of peaks and valleys or inter-peaks regions in profile. In any event, each notch may represent a decrease in crest height (and/or a gap) of a helical ridge between successive teeth. The notch in profile may be arcuate, angular (e.g., at least generally V-shaped), linear, or the like. The crest of a nonserrated thread is shown in dashed outline at 68 for comparison.

FIG. 8 shows a magnified portion of FIG. 7. Winding 28 may include a continuous helical ridge 70 forming a succession of teeth 66. In other words, adjacent teeth 66 may be connected to one another not only by root portion 46 but also by a portion (e.g., a notched portion) of helical ridge 70 that is elevated from root portion 46. As a result, the serrated thread of this particular embodiment may have a greater mechanical stability and may remain locked under a greater load, when compared to an interrupted (gapped) thread in which portions of the thread are completely removed or omitted down to the root portion.

Components of the bone plate system may be formed of any suitable biocompatible and/or bioresorbable materials. Exemplary materials are disclosed in U.S. patent application Ser. No. 12/616,054, filed Nov. 10, 2009, which is incorporated herein by reference. In exemplary embodiments, the bone plate and bone screw are each formed of metal. In some examples, the bone plate and the bone screw may have about the same hardness (and/or malleability) and/or may be formed of about the same metal alloy, such that both the bone plate and the screw are deformed substantially when the screw is installed in a cross-threaded configuration. For example, both may be formed of titanium (e.g., a titanium alloy) and/or both may be formed of stainless steel, among others. In other examples, the bone plate may be harder and/or less malleable than the bone screw, or vice versa. For example, the bone plate may be formed of titanium (e.g., a titanium alloy) and the bone screw of stainless steel, or vice versa.

II. EXEMPLARY FIXATION AND ATTACHMENT METHODS

This section describes exemplary methods of utilizing the bone plate systems disclosed herein to fix bone, to attach a bone plate to bone, and/or to attach a fastener to a bone plate. The steps described herein may be performed in any suitable order, in any suitable combination, and may be combined with any other steps described elsewhere in the present disclosure.

A bone plate and one or more fasteners may be selected. The bone plate may define a plurality of apertures, at least one of which has an internal thread. The aperture also may have a counterbore formed above the internal thread. The counterbore may form a ledge which against a fastener can be seated. The fastener may have any combination of the features disclosed herein, such as a proximal region tapering toward a distal region, and serrated thread in the proximal region.

At least one bone may be selected for fixation with or attachment to the bone plate, and/or for receiving the fastener. The bone(s) may have any suitable condition, such as a fracture, an osteotomy, a malunion, arthritis in a joint formed between a pair of selected bones (e.g., bones to be fused with the fastener), a structural instability, or the like. A bone from any part of the skeleton may be selected. Exemplary bones include a bone of the arms (such as a humerus, a radius, and/or an ulna), a bone of the legs (such as a femur, a tibia, and/or a fibula), a bone of the hands (such as a carpal, metacarpal, and/or phalange), a bone of the feet (such as a tarsal, metatarsal, and/or phalange), a clavicle, a rib, a scapula, a pelvic bone, a vertebra, a skull, a mandible, or the like.

The bone plate may be disposed on the selected bone(s). In some examples, the bone plate may be disposed to span a discontinuity formed in the bone, such as a fracture or a cut, among others.

A trajectory having an angle with respect to the aperture axis may be selected for placement of the selected fastener. The trajectory may correspond to an angle of zero between the axes of the aperture and fastener, such that the fastener and the aperture are in a co-axial arrangement, or may provide an angle of greater than zero, such that the fastener is in a skewed arrangement with respect to the aperture. A hole may be drilled coaxial to the selected trajectory of the fastener. Alternatively, the fastener may be configured to be self-drilling.

The fastener may be disposed in the aperture and in the bone with the selected trajectory and at the selected angle. If a skewed arrangement was selected, the serrated thread may be cross-threaded with the internal thread to create an interference fit and locked engagement of the proximal region with the aperture. If a coaxial arrangement was selected, the serrated thread may be disposed in threaded engagement with the internal thread to lock the fastener to the aperture without cross-threading. With either arrangement, the fastener may be wedged into the aperture as it is advanced. In any event, one or more additional fasteners, such as bone screws, also may be installed to secure the bone plate to bone.

III. EXAMPLES

This section describes further aspects of exemplary bone plate systems including a bone screw with an external serrated thread. These examples are included for illustration and are not intended to limit or define the entire scope of the present disclosure.

Example 1

Exemplary Bone Screw with an Undercut Head

This example describes an exemplary bone screw 80 having a head 82 that is circumferentially undercut; see FIG. 9.

Head 82 may include a flange that forms a ledge 84 proximal to serrated thread 86. The ledge may act as a stop that restricts advancement of the bone screw during installation. For example, the ledge may engage a wall of the bone plate aperture, such as a shoulder or ledge 90 formed at the base of the aperture's counterbore (see FIG. 2). Head 82 may engage shoulder 90 circumferentially when the screw is inserted coaxially and may engage the shoulder selectively on only one side when the screw is inserted in a skewed orientation (off-axis).

Example 2

Exemplary Bone Screw with Discrete Proximal and Distal Threads

Figure 10:
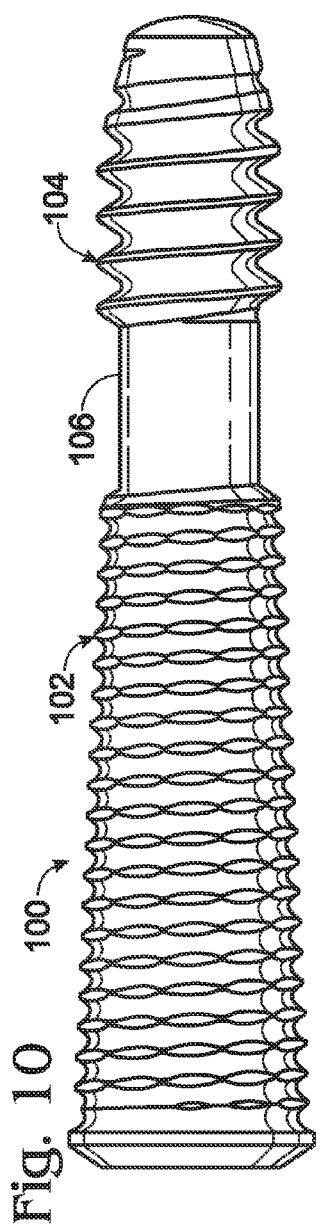
FIG. 10 is a side view of yet another exemplary bone screw that may be utilized in the bone plate system of FIG. 1, in accordance with aspects of the present disclosure.

This example describes an exemplary bone screw 100 having discrete proximal and distal threads 102, 104 that are spaced from each other; see FIG. 10.

The discrete threads may have any suitable structure. For example, the threads may have different pitches, different heights above the shaft, or both. Alternatively, or in addition, the discrete threads may be separated by a nonthreaded region 106 of the shaft.

Example 3

Exemplary Bone Screw with Tapered Thread

Figure 11:
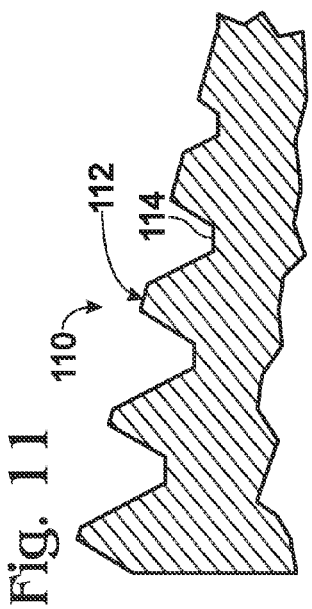
FIG. 11 is a fragmentary, longitudinal sectional view of still yet another exemplary bone screw that may be utilized in the bone plate system of FIG. 1, in accordance with aspects of the present disclosure.

This example describes an exemplary bone screw 110 having a serrated thread 112 that generally tapers in height; see FIG. 11.

Serrated thread 112 may taper in a distal direction at a distinct angle from a taper angle of a root portion 114 of the screw. For example, as shown here, the crest of the serrated thread may define a steeper angle than the taper angle of root portion 114, such that the average height or tooth height of the serrated thread decreases in a distal direction.

Example 4

Exemplary Bone Plate System for the Distal Radius

Figure 12:
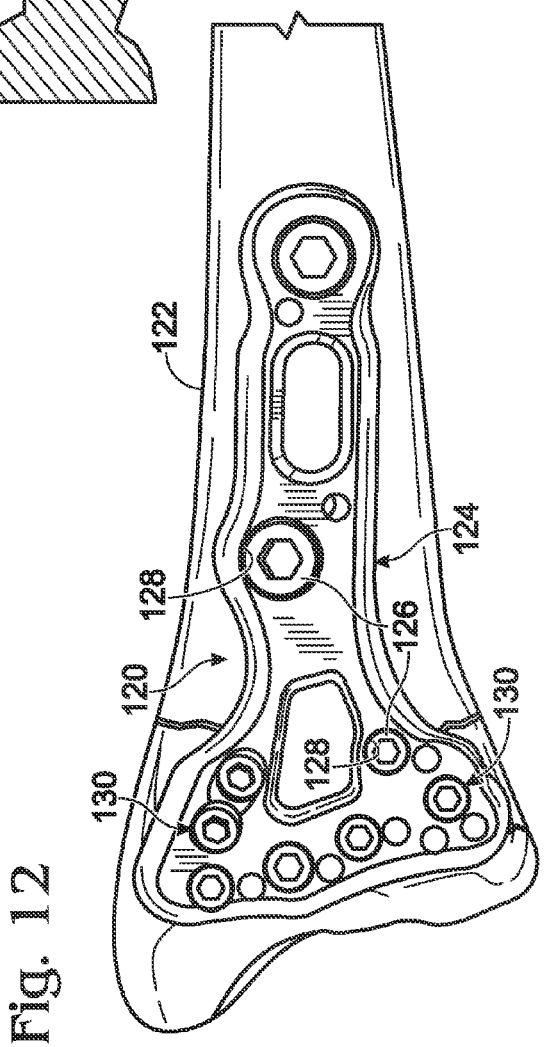
FIG. 12 is a volar view of a distal region of a fractured radial bone fixed with an exemplary bone plate that is attached to the radial bone with a pair of the bone screws of FIG. 9, in accordance with aspects of the present disclosure.

This example describes an exemplary bone plate system 120 for fixation of a distal region of a radial bone 122; see FIG. 12.

System 120 may include a bone plate 124 and a plurality of fasteners, namely, bone screws 126 for fastening the bone plate to bone 122. The bone plate may define apertures 128 that receive the bone screws. Any one or combination of the apertures may be designed to receive a bone screw at a selectable angle, as disclosed herein. Furthermore, any of bone screws 126 may be structured to include a serrated thread and/or a tapered proximal region as disclosed herein. In some embodiments, one or both of the apertures indicated at 130 may be utilized to receive a bone screw as disclosed herein at a selectable angle.

Example 5

Selected Embodiments I

This example describes selected embodiments of a bone plate system, listed as a series of numbered paragraphs.

1. A system for bone fixation, comprising: (A) a bone plate defining an aperture including an internal thread; and (B) a fastener defining a long axis and including a proximal region and a distal region, the proximal region being tapered conically toward the distal region with an angle of taper of about one to five degrees with respect to the long axis and including a serrated thread, the fastener being insertable into the aperture in a coaxial arrangement with the aperture to achieve threaded engagement of the serrated thread with the internal thread without cross-threading and being insertable in a skewed arrangement to provide an interference fit and locked engagement of the proximal region with the aperture by cross-threading the serrated thread and the internal thread.

2. The system of paragraph 1, wherein the proximal region has a greater angle of taper than a threaded region of the aperture that includes the internal thread.

3. The system of paragraph 1 or paragraph 2, wherein the proximal region forms an angle of taper of about two to four degrees with respect to the long axis.

4. The system of any preceding paragraph, wherein the serrated thread forms a plurality of teeth, wherein each tooth has a top where a height of the tooth is at a maximum for such tooth, and wherein the tops of all of the teeth of the serrated thread collectively represent less than one-half of a total length of the serrated thread as measured along a path followed by the serrated thread around the long axis.

5. The system of any preceding paragraph, wherein the serrated thread forms a plurality of teeth, wherein each tooth has a top where a height of the tooth is at a maximum for such tooth, and wherein the serrated thread includes a plurality of notches with each notch disposed between an adjacent pair of tops of the teeth.

6. The system of paragraph 5, wherein each notch has an arcuate profile.

7. The system of any preceding paragraph, wherein a height of the serrated thread progressively decreases and increases multiple times in alternation for each full winding of the serrated thread around the long axis.

8. The system of any preceding paragraph, wherein the distal region of the fastener includes a thread.

9. The system of paragraph 8, wherein the thread of the distal region and the serrated thread follow different parts of a same helical path.

10. The system of paragraph 8 or paragraph 9, wherein the thread of the distal region and the serrated thread have a same pitch.

11. The system of any one of paragraphs 8 to 10, wherein the thread of the distal region is not serrated substantially.

12. The system of any one of paragraphs 8 to 11, wherein the serrated thread and the thread of the distal region collectively are formed on a majority of the length of the fastener.

13. The system of any preceding paragraph, wherein a height of the serrated thread varies continuously along at least a majority of a total length of the serrated thread as measured along a path followed by the serrated thread around the long axis.

14. The system of any preceding paragraph, wherein a region of the aperture that includes the internal thread is cylindrical.

15. The system of any preceding paragraph, wherein the bone plate has an inner surface region that is contoured to fit onto a distal surface region of a radial bone.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of attaching a fastener to a bone plate, comprising:
    selecting (i) a bone plate defining an aperture having an internal thread and (ii) a fastener defining a long axis and including a proximal region and a distal region, the proximal region having a conical portion with an angle of taper toward the distal region of about one to five degrees with respect to the long axis, the conical portion including a thread having a serrated portion; and
    disposing the fastener in the aperture and in bone, such that the thread of the conical portion is cross-threaded with the internal thread to attach the proximal region to the aperture.

2. The method of claim 1, wherein the thread of the conical portion is configured to provide threaded engagement with the internal thread without cross-threading, if the fastener is arranged coaxially with the aperture.

3. The method of claim 1, wherein the serrated portion forms a plurality of teeth, wherein each tooth has a top where a height of the tooth is at a maximum for such tooth, and wherein the tops of all of the teeth of the serrated portion collectively represent less than one-half of a total length of the serrated portion as measured along a path followed by the serrated portion around the long axis.

4. The method of claim 1, wherein the serrated portion forms a plurality of teeth, wherein each tooth has a top where a height of the tooth is at a maximum for such tooth, and wherein the serrated portion includes a plurality of notches with each notch disposed between an adjacent pair of tops of the teeth.

5. The method of claim 4, wherein each notch has an arcuate profile.

6. The method of claim 1, wherein a height of the serrated portion progressively decreases and increases multiple times in alternation along each complete winding of the serrated portion around the long axis.

7. The method of claim 1, wherein the distal region includes a thread, and wherein the step of disposing includes a step of disposing the thread of the distal region in threaded engagement with the bone.

8. The method of claim 7, wherein the thread of the distal region and the thread of the conical portion follow different parts of a same helical path.

9. The method of claim 7, wherein the thread of the distal region and the thread of the conical portion have a same pitch.

10. The method of claim 7, wherein the thread of the distal region is not serrated substantially.

11. The method of claim 1, wherein a region of the aperture that includes the internal thread has a smaller angle of taper, if any, than the conical portion of the fastener, and wherein the step of disposing includes a step of wedging the conical portion into the region of the aperture as the fastener is turned.

12. The method of claim 1, wherein a height of the serrated portion varies continuously along at least a majority of a total length of the serrated portion as measured along a path followed by the serrated portion around the long axis.

13. A method of attaching a fastener to a bone plate, comprising:

selecting a bone plate defining an aperture having a region that includes an internal thread;

selecting a fastener including a proximal region and a distal region, the proximal region having a conical portion, the conical portion being tapered toward the distal region with a larger angle of taper than the region of the aperture and including a first thread having a serrated portion, the first thread of the conical portion being configured to be disposed in threaded engagement with the internal thread of the aperture without cross-threading, if the fastener and the aperture are coaxial to each other, the distal region being cylindrical and including a second thread; and disposing the fastener in the aperture and in bone, such that the proximal region is wedged into the region of the aperture and the first thread is cross-threaded with the internal thread, to attach the proximal region to the aperture.

14. The method of claim 13, wherein the conical portion forms an angle of taper of about one to five degrees with respect to a long axis defined by the fastener.

15. The method of claim 14, wherein the conical portion forms an angle of taper of about two to four degrees with respect to the long axis.

16. The method of claim 13, wherein the serrated portion defines a plurality of arcuate notches that form teeth among the notches.

17. The method of claim 13, wherein the region of the aperture is not tapered.

18. The method of claim 13, wherein the first thread is continuous with the second thread.

19. The method of claim 13, wherein the serrated portion includes a plurality of teeth, and wherein the step of disposing deforms one or more of the teeth.

20. A system for bone fixation, comprising:
a bone plate defining an aperture having an internal thread; and
a fastener defining a long axis and including a proximal region and a distal region, the proximal region having a conical portion with an angle of taper toward the distal region of about one to five degrees with respect to the long axis, the conical portion including a thread having a serrated portion, the fastener being insertable into the aperture in a coaxial arrangement with the aperture to achieve threaded engagement of the thread of the conical portion with the internal thread without cross-threading and being insertable in a skewed arrangement to attach the proximal region to the aperture by cross-threading the thread of the conical portion and the internal thread.

21. A method of attaching a fastener to a bone plate, comprising:
selecting (i) a bone plate defining an aperture having an internal thread and (ii) a fastener defining a long axis and including a proximal region and a distal region, the proximal region being conical with an angle of taper toward the distal region of about one to five degrees with respect to the long axis and including a serrated thread; and
disposing the fastener in the aperture and in bone, such that the serrated thread is cross-threaded with the internal thread to create an interference fit and locked engagement of the proximal region with the aperture,
wherein the serrated thread of the fastener selected forms a plurality of teeth, wherein each tooth has a top where a height of the tooth is at a maximum for such tooth, and wherein the tops of all of the teeth of the serrated thread collectively represent less than one-half of a total length of the serrated thread as measured along a path followed by the serrated thread around the long axis.

22. A method of attaching a fastener to a bone plate, comprising:
selecting (i) a bone plate defining an aperture having an internal thread and (ii) a fastener defining a long axis and including a proximal region and a distal region, the proximal region being conical with an angle of taper toward the distal region of about one to five degrees with respect to the long axis and including a serrated thread; and
disposing the fastener in the aperture and in bone, such that the serrated thread is cross-threaded with the internal thread to create an interference fit and locked engagement of the proximal region with the aperture,
wherein the serrated thread of the fastener selected forms a plurality of teeth, wherein each tooth has a top where a height of the tooth is at a maximum for such tooth, and wherein the serrated thread includes a plurality of notches with each notch disposed between an adjacent pair of tops of the teeth.

23. A method of attaching a fastener to a bone plate, comprising:
selecting (i) a bone plate defining an aperture having an internal thread and (ii) a fastener defining a long axis and including a proximal region and a distal region, the proximal region being conical with an angle of taper toward the distal region of about one to five degrees with respect to the long axis and including a serrated thread; and
disposing the fastener in the aperture and in bone, such that the serrated thread is cross-threaded with the internal thread to create an interference fit and locked engagement of the proximal region with the aperture,
wherein a height of the serrated thread of the fastener selected progressively decreases and increases multiple times in alternation along each complete winding of the serrated thread around the long axis.

24. A method of attaching a fastener to a bone plate, comprising:
selecting (i) a bone plate defining an aperture having an internal thread and (ii) a fastener defining a long axis and including a proximal region and a distal region, the proximal region being conical with an angle of taper toward the distal region of about one to five degrees with respect to the long axis and including a serrated thread; and
disposing the fastener in the aperture and in bone, such that the serrated thread is cross-threaded with the internal thread to create an interference fit and locked engagement of the proximal region with the aperture,
wherein a height of the serrated thread of the fastener selected varies continuously along at least a majority of a total length of the serrated thread as measured along a path followed by the serrated thread around the long axis.

* * * * *